(12) United States Patent
Rock et al.

(10) Patent No.: US 6,575,914 B2
(45) Date of Patent: Jun. 10, 2003

(54) INTEGRATED CARDIAC RESUSCITATION SYSTEM WITH ABILITY TO DETECT PERFUSION

(75) Inventors: Joseph E. Rock, Littleton, MA (US); Michael Nakagawa, Cambridge, MA (US); Catherine Rochford, Atkinson, NH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 60 days.

(21) Appl. No.: 09/860,366

(22) Filed: May 18, 2001

(65) Prior Publication Data

US 2002/0173725 A1 Nov. 21, 2002

(51) Int. Cl.[7] ............................. A61B 5/02; A61B 5/00
(52) U.S. Cl. ...................... 600/500; 483/509; 483/301; 607/9; 607/6; 607/17
(58) Field of Search .................... 600/500, 506, 600/528, 483, 509, 300, 301; 607/9, 17, 19, 24, 25, 3–7, 26, 33

(56) References Cited

U.S. PATENT DOCUMENTS

| 4,088,138 | A |   | 5/1978  | Diack et al.        |
|-----------|---|---|---------|---------------------|
| 4,424,814 | A |   | 1/1984  | Secunda             |
| 4,770,184 | A |   | 9/1988  | Greene, Jr. et al.  |
| 4,955,381 | A |   | 9/1990  | Way et al.          |
| 5,080,099 | A |   | 1/1992  | Way et al.          |
| 5,316,001 | A |   | 5/1994  | Ferek-Petric et al. |
| 5,511,553 | A | * | 4/1996  | Segalowitz ............. 218/696 |
| 5,951,598 | A |   | 9/1999  | Bishay et al. ............ 607/142 |
| 5,991,661 | A | * | 11/1999 | Park et al. ................ 607/9 |
| 6,144,866 | A |   | 11/2000 | Miesel et al.       |
| 6,149,587 | A |   | 11/2000 | Raines              |
| 6,440,082 | B1 | * | 8/2002 | Joo et al. ................. 600/528 |

FOREIGN PATENT DOCUMENTS

| DE | 10008886 A   | 9/2001 |
| EP | 0947163 A2   | 6/1999 |
| EP | 1057498 A2   | 6/2000 |
| WO | WO 94/04073  | 3/1994 |

* cited by examiner

Primary Examiner—Mark Paschall

(57) ABSTRACT

A system and method includes a cardiac resuscitation apparatus connected to an automated external programmable defibrillator (AED) or a semi-automated external programmable defibrillator (SAED) includes an adhesive Doppler pad to detect a pulse signal of a patient. Defibrillation-monitoring pads are connected to the Doppler pad and detect an ECG signal of the patient. A processor integrates the pulse signal and the ECG signal to determine therefrom whether or not shock therapy is advised for the patient.

47 Claims, 7 Drawing Sheets

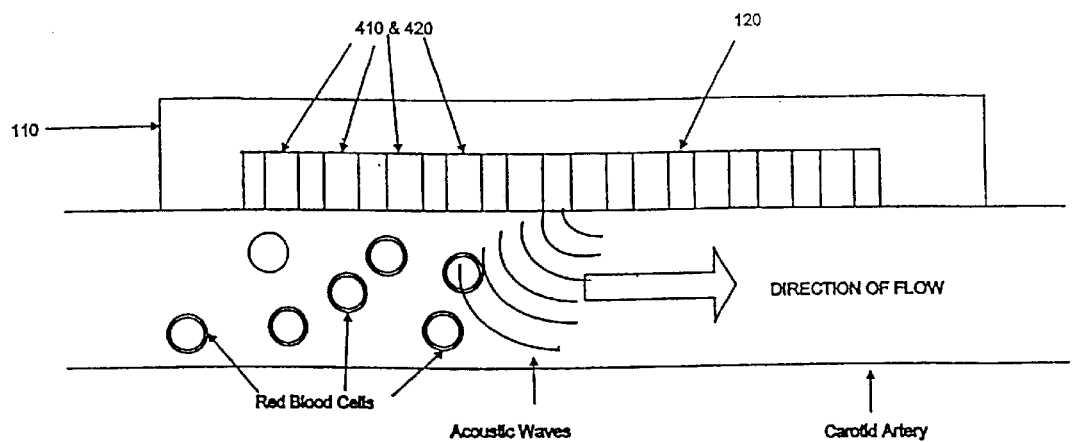
FIG. 5A Transducer Transmitting
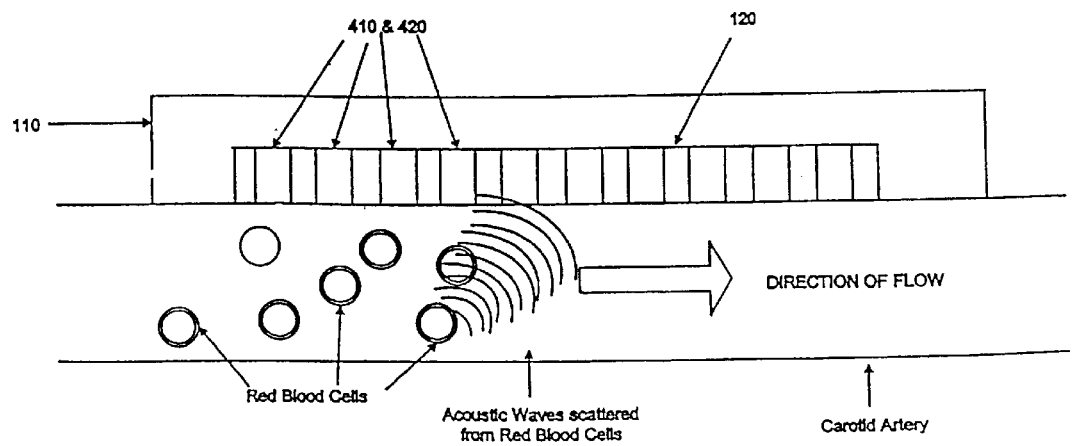
FIG. 5B Transducer Receiving

US 6,575,914 B2

INTEGRATED CARDIAC RESUSCITATION SYSTEM WITH ABILITY TO DETECT PERFUSION

BACKGROUND OF THE INVENTION

Ventricular fibrillation is characterized by rapid electrical impulses to the ventricles, incomplete ventricular contractions, and resultant loss of pulse and blood pressure. Defibrillating the patient depends upon identifying the situation by emergency rescuers who typically work under chaotic conditions and time pressures. Thus, delaying defibrillating may be harmful to the patient and result in long-term complications and or death.

The American Heart Association protocol for cardiopulmonary resuscitation (CPR) requires a healthcare professional to assess the patient's pulse for five to ten seconds. Lack of a pulse is an indication for the commencement of external chest compressions. Assessing the pulse, while seemingly simple on a conscious adult, is the most often failed component of a basic life support assessment sequence, which may be attributed to a variety of reasons, such as lack of experience, poor landmarks, or a bias to either finding or not finding a pulse. Failure to accurately detect the presence or absence of the pulse will lead to adverse treatment of the patient either when providing or not providing CPR or defibrillation therapy to the patient.

Electrocardiogram (ECG) signals are normally used to determine whether or not a defibrillating shock should be applied. However, certain rhythms that a rescuer is likely to encounter cannot be determined solely by the ECG signal, e.g. non-perfusing ventricular tachycardia or pulseless electrical activity; diagnoses of these rhythms require supporting evidence of a lack of perfusion despite the myocardial electrical activity as indicated by the ECG signal.

Currently, clinicians use standalone Doppler systems to detect the patient's pulse and to measure blood flow. Once the information is gathered by the Doppler system and processed, the rescuer then needs to gather the ECG signals and make a determination whether to defibrillate the patient. Furthermore, while the rescuer is performing CPR, the rescuer has no means of assessing the adequacy of perfusion, that is, whether the amount of blood flow is adequate. Because the pulse check or blood flow measurement is performed manually, it is subject to human error, and in an emergency situation where time is of the essence, the amount of time to gather the information before beginning the ECG signal analysis to determine whether to defibrillate the patient or continue CPR is too long thereby causing detrimental results. Also, this procedure is costly because of the need to purchase and maintain a separate piece of equipment.

Furthermore, although Doppler systems have been implemented to detect an infant's heartbeat, these Doppler systems have not been optimized for detecting perfusion and obtaining the patient's pulse to determine whether to defibrillate the patient. Thus, it is necessary to develop an integrated system that is quickly and easily able to determine the patient's pulse, measure the amount of blood flow, and determine the ECG signals to make an accurate and adequate determination whether to defibrillate the patient.

SUMMARY OF THE INVENTION

In an exemplary embodiment, the present invention provides for a noninvasive cardiac resuscitation system including a cardiac resuscitation pad set integrating defibrillation-monitoring pads, which determines whether the patient's heart is undergoing a shockable rhythm, and a Doppler pad. The Doppler pad is adhesively secured to a patient's skin to sense the carotid pulse in the carotid artery which has been found as a key indicator of sufficient cerebral perfusion. The Doppler pad is adhesively secured to the patient in proximity to the carotid artery maintaining stability over the carotid artery and adequately isolating the system from noise caused transducer movement. Further, the Doppler pad integrates a transducer including one of multiple transmitters and receivers, a single transmitter and multiple receivers, and multiple transmitters and a single receiver covering a large area of the patient's neck overlaying the carotid artery. Thus, the cardiac resuscitation system including the cardiac resuscitation pad set, in accordance with the present invention, provides an emergency rescuer with a high degree of certainty in obtaining a pulse reading, measuring the velocity of blood flowing through a vessel, and whether it is appropriate to defibrillate the patient.

In an exemplary embodiment, the present invention provides a cardiac resuscitation apparatus including an adhesive Doppler pad detecting a pulse signal; and defibrillation-monitoring pads, connected to the Doppler pad, detecting an ECG signal, wherein the pulse signal and the ECG signal are integrated to determine whether or not shock therapy is advised for a patient. The present invention also provides for a cardiac resuscitation apparatus including an adhesive Doppler pad including one of multiple transmitters and receivers, a single transmitter and multiple receivers, and multiple transmitters and a single receiver integrated therein detecting a pulse signal of a patient; defibrillation-monitoring pads detecting an ECG signal of the patient, wherein the adhesive Doppler pad and the defibrillation-monitoring pads are connected to the cardiac resuscitation apparatus via a single conductive cable; and a processor integrating the pulse signal and the ECG signal and determining therefrom if a pulse of the patient is present, measuring blood flow, and whether a shockable rhythm is present.

The present invention is also achieved by providing a method in a cardiac resuscitation system that includes detecting a pulse signal of a patient; detecting an ECG signal of the patient; integrating the pulse signal and the ECG signal; and determining from the integrated signals whether or not shock therapy is advised to a patient. A method in a cardiac resuscitation system includes connecting an adhesive Doppler pad and defibrillation-monitoring pads to an Automatic External Defibrillators (AEDs) or a Semi-Automatic External Defibrillators (SAEDs) via a single conductive cable; detecting a pulse signal of a patient via the adhesive Doppler pad including one of multiple transmitters and receivers, a single transmitter and multiple receivers, and multiple transmitters and a single receiver integrated therein; detecting an ECG signal of the patient via the defibrillation-monitoring pads; and integrating the pulse signal and the ECG signal and determining therefrom if a pulse is present, measuring blood flow, and determining whether a shockable rhythm is present.

The present invention is also achieved by providing a computer readable storage controlling a computer in a cardiac resuscitation system and including a process of positioning an adhesive Doppler pad relative to a carotid artery of a patient to monitor a pulse signal; positioning defibrillation-monitoring pads on the patient to monitor a shockable rhythm analysis result; integrating the pulse signal and the shockable rhythm; determining shock therapy is not advised for a patient when the integrated signal indicates that a pulse is detected or a shockable rhythm is not detected; and determining that shock therapy is advised for the patient when the integrated signal indicates that the pulse is not detected and the shockable rhythm is detected.

BRIEF DESCRIPTION OF THE DRAWINGS

The various objects and advantages of the invention will become apparent and more readily appreciated from the following description of the preferred embodiments, taken in conjunction with the accompanying drawings of which:

FIG. 5A is a diagram illustrating a cross-sectional view of the Doppler pad placed over a carotid artery transmitting signals;

FIG. 5B is a diagram illustrating a cross-sectional view of the Doppler pad placed over the carotid artery receiving return signals;

DESCRIPTION OF THE PREFERRED EMBODIMENTS

Figure 1:
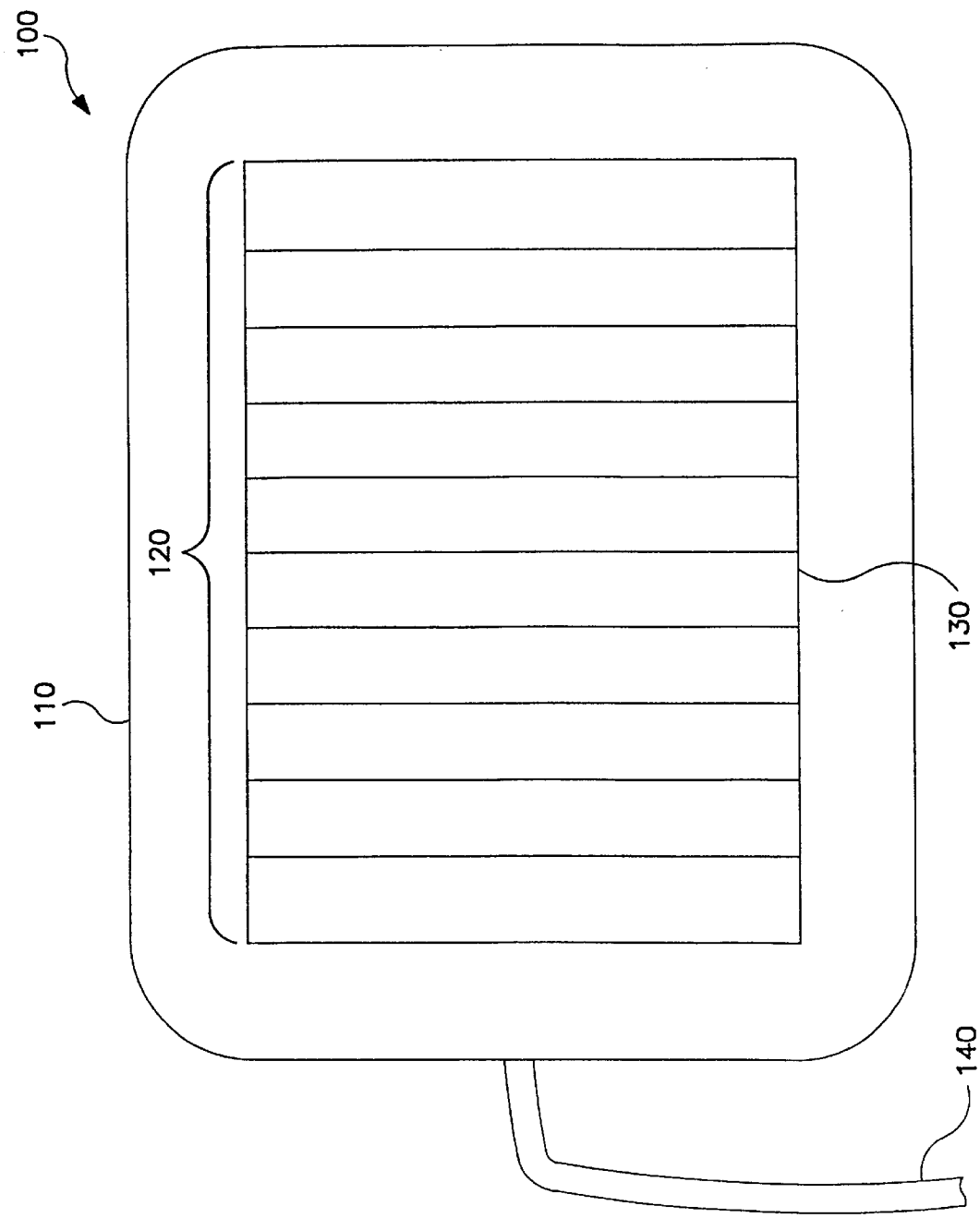
FIG. 1 is a diagram illustrating a noninvasive adhesive Doppler pad, in an exemplary embodiment of the present invention.

Reference will be now made in detail to the present preferred embodiments of the present invention, examples of which are illustrated in the accompanying drawings, wherein like reference numerals refer to the like elements throughout.

The present invention provides for a noninvasive cardiac resuscitation system including a cardiac resuscitation pad set including three conductors terminating in two defibrillation-monitoring pads and an adhesive Doppler pad. The Doppler pad includes a piezoelectric transducer that generates continuous waves (CW) at a constant frequency and receives waves that have been scattered by red blood cells flowing through the carotid artery. The waves received are then sent to a processor which calculates the associated Doppler shift and analyzes the frequency information to determine the presence or absence of the patient's carotid pulse, which is the diagnostic test for cardiac arrest, and a duration of the pulse, if any, which is indicative of blood flow of the patient. The defibrillation-monitoring pads sense electrocardiogram (ECG) parameters, such as a shockable rhythm, and are used to apply defibrillation therapy. The Doppler pad generates a signal indicative of the patient's arterial blood flow and, thereby, pulse to a defibrillator. The ECG parameters and the pulse signals are integrated and whether defibrillation therapy should be applied to the patient is determined therefrom. Specifically, integration is defined as the noninvasive cardiac resuscitation system waiting to receive both, the ECG parameters and the pulse signals, if any, prior to making a determination therefrom whether the defibrillation therapy should be applied to the patient. Integrating the noninvasive cardiac resuscitation pad set in an Automatic External Defibrillators (AED) or a Semi-Automatic External Defibrillators (SAED) provides for a system that is inexpensive and easy to use.

Referring to FIG. 1, this figure illustrates the Doppler pad 100 as an integrated unit in accordance with an exemplary embodiment of the present invention. An adhesive pad 110 and a piezoelectric transducer 120 including multiple piezoelectric elements 130 are integrated in the Doppler pad 100. The piezoelectric transducer 120 is a flexible material which when energized produces mechanical stress. Although a piezoelectric transducer is illustrated in the exemplary embodiment, an ordinary person skilled in the art will appreciate that any other type of component or material that exhibits piezoelectric attributes may be used so that when the material is energized it produces a mechanical effect. The piezoelectric transducer 120 includes multiple piezoelectric elements 130 to generate CW signals or, in the alternative, pulse signals, and phased array modalities to detect or to receive the patient's pulse and to determine the blood flow to be later processed. A conductor 140 connects the Doppler pad 100 to a defibrillator (not shown).

In accordance with the present invention, directly adhering the Doppler pad 100 onto the patient prevents movement of the Doppler pad 100 while sensing the Doppler energy in the carotid artery thereby isolating the Doppler pad 100 from sensing false Doppler energy generated because of transducer movement. Further, the adhesiveness of the Doppler pad 100 provides the rescuer with a degree of freedom. Specifically, the rescuer may place the Doppler pad 100 on the patient without having to hold it in place while taking the pulse, and future pulse checks can be performed without further attention to the transducer assembly.

Figure 2:
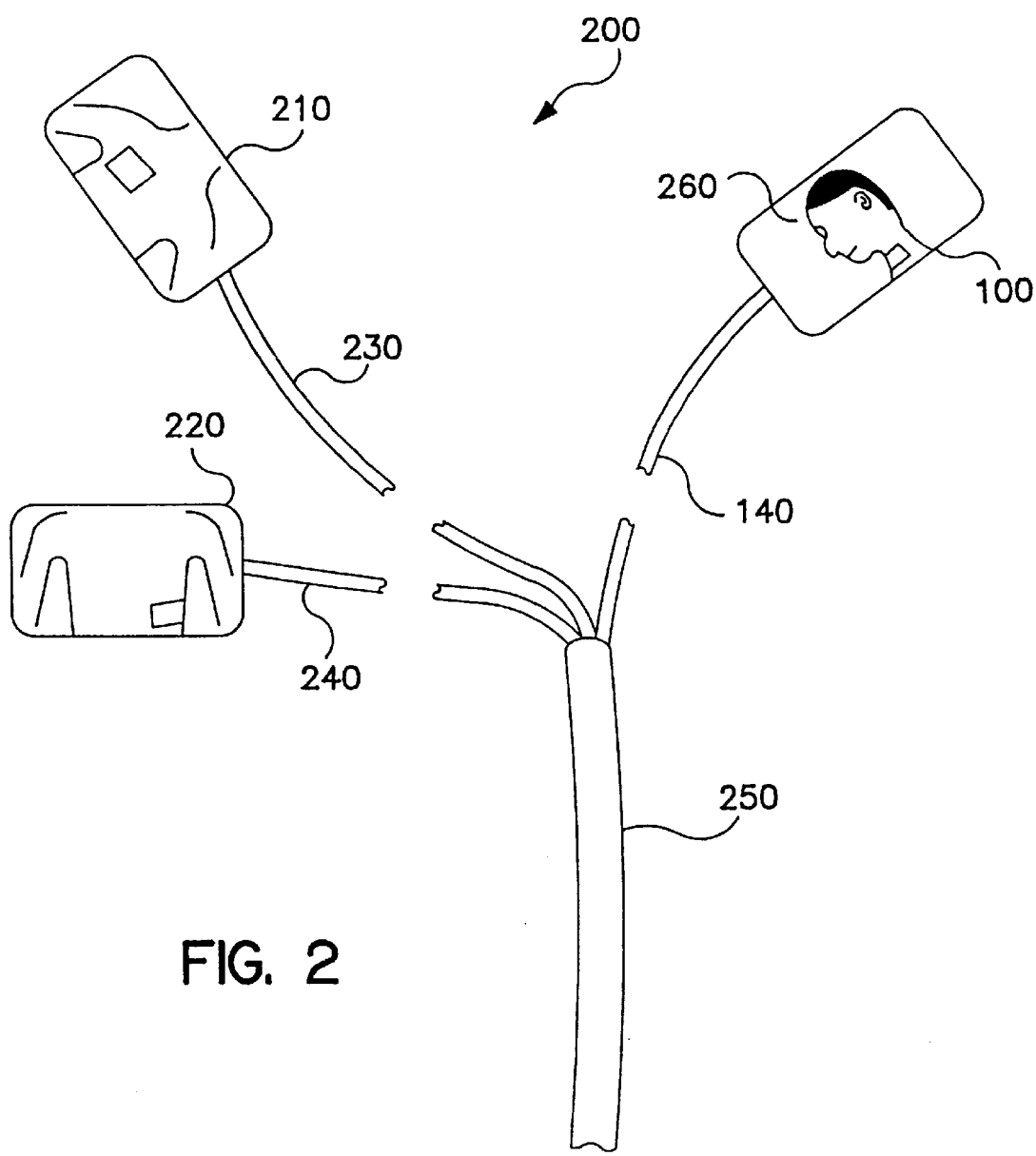
FIG. 2 is a diagram illustrating a cardiac resuscitation system including a cardiac resuscitation pad set, in accordance with an exemplary embodiment of the present invention.

Referring to FIG. 2, this figure illustrates a cardiac resuscitation system 200 including the cardiac resuscitation pad set connected to the defibrillator (not shown), in accordance with an exemplary embodiment of the present invention. The cardiac resuscitation pad set includes the Doppler pad 100 and defibrillation-monitoring pads 210, 220. The conductors 140, 230, 240 from the Doppler pad 100 and the defibrillation-monitoring pads 210, 220 are connected into a single conductive cable 250 thereby connecting the defibrillation-monitoring pads 210, 220 and the Doppler pad 100 to the defibrillator as a unit. Furthermore, in order to facilitate and assure proper placement of the Doppler pad 100 and the defibrillation-monitoring pads 210, 220, a pictorial instruction is included on each pad providing guidance to the user as to placement of the pad on the patient. For instance, each of the defibrillation-monitoring pads 210, 220 would include a picture of a human torso and physically show where on the torso each defibrillation-monitoring pads 210, 220 should be placed. Similarly, the Doppler pad 100 would include a diagram of the patient's neck, jaw line, and tip of an earlobe and some orientation of the neck.

Figure 3:
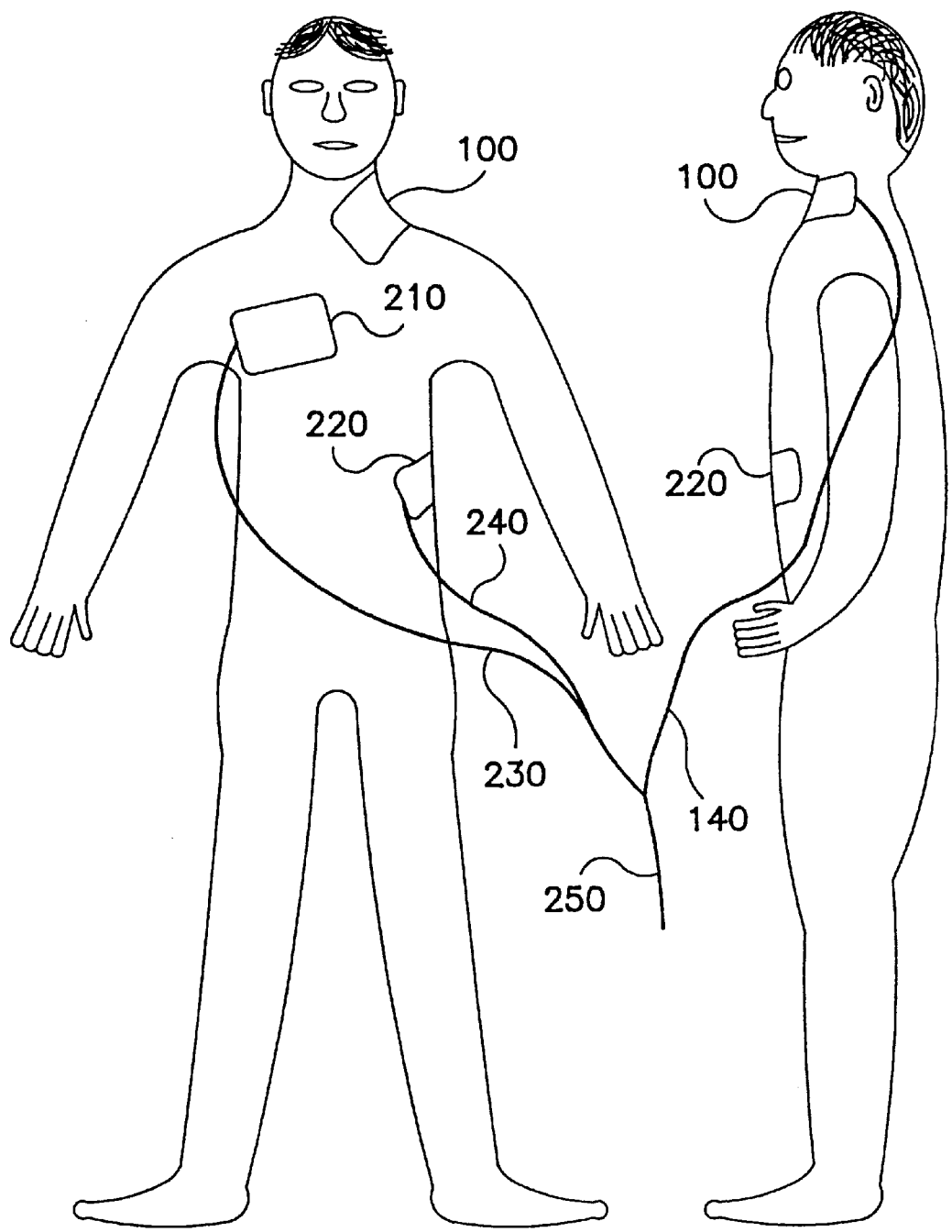
FIG. 3 is a diagram illustrating placement of the cardiac resuscitation pad set on a patient.

Referring to FIG. 3, this figure shows the placement of the cardiac resuscitation pad set including the defibrillation-monitoring pads 210, 220 and the Doppler pad 100 on a patient and the single conductive cable 250 connecting the defibrillation-monitoring pads 210, 220 and the Doppler pad 100 to the defibrillator. In an exemplary embodiment, the rescuer places the defibrillation-monitoring pads 210, 220 on the patient. The Doppler pad 100 is adhesively placed on the carotid artery to sense the carotid pulse to detect if there is sufficient cerebral perfusion and a duration of which is indicative of blood flow of the patient. The rescuer subsequently turns on the defibrillator. Upon detecting the patient, the defibrillator receives from the Doppler pad 100 the Doppler signal indicative of the patient's pulse. The defibrillation-monitoring pads 210, 220 provide the defibrillator the ECG signal indicative of whether the patient's heart is undergoing a shockable rhythm and is also used to to apply defibrillation therapy on the patient, if necessary. The defibrillator integrates both signals and determines therefrom if a pulse is present, the blood flow, and whether a shockable rhythm is present. If during the analysis of the ECG signal and the Doppler signal a shockable rhythm is detected and a pulse is not present, the defibrillator would charge an energy storage capacitor (not shown) in anticipation of applying a defibrillation pulse to the patient.

Figure 4:
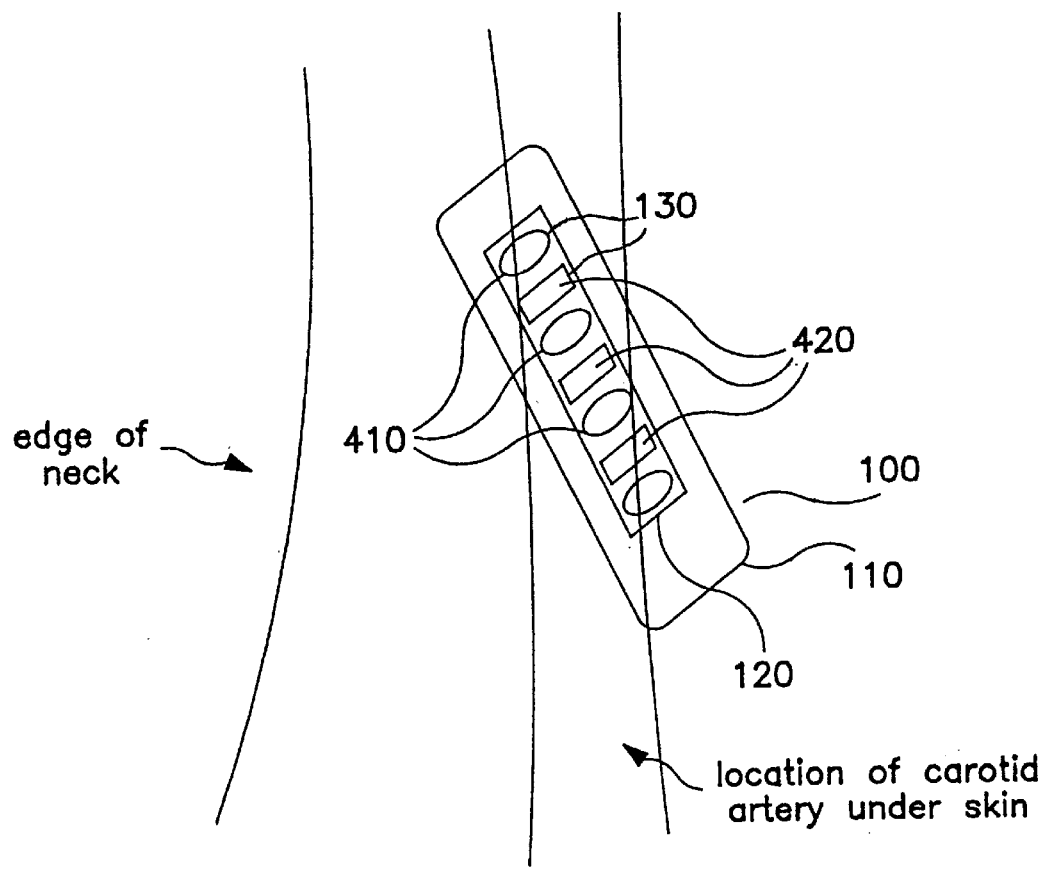
FIG. 4 is a diagram illustrating the Doppler pad secured to the patient's neck including an adhesive pad, a transducer, and piezoelectric elements, in accordance with an exemplary embodiment of the present invention.

Referring to FIG. 4, this figure illustrates a detailed embodiment of the Doppler pad 100 secured to the patient's neck including the adhesive pad 110, the transducer 120, and the piezoelectric elements 130 of the transducer 120 including multiple transmitters/receivers 410, 420. The transmitters/receivers 410, 420 are used to account for potential misalignment of the transducer 120 with respect to the carotid artery. The transmitters/receivers 410, 420 are mounted within the Doppler pad 100 at a predetermined orientation with respect to the patient's skin surface. In the alternative, a single transmitter and multiple receivers or multiple transmitters and a single receivers may be mounted within the Doppler pad 100. A person of ordinary skill in the art will appreciate that, although the transmitters/receivers 410,420 are illustrated as having an oval or rectangular shape, these shapes are for illustrative and clarity purposes only, and further, the transmitters 410 may be used as receivers 420. As previously mentioned, the Doppler pad 100 would include a schematic diagram of the proper placement of the Doppler pad 100 on the patient's neck.

It is desirable to orient the transmitters/receivers 410, 420 in the transducers so that the blood flow up the carotid artery into the brain is parallel to the orientation of the transmitters/receivers 410, 420. Present standalone Doppler systems include a single transmitter/receiver. As a result, if the position of the transmitter/receiver is off-angle with respect to the blood flow, it is not possible for the Doppler system to correct for the misplacement.

In contrast, in accordance with an exemplary embodiment of the present invention, because the transducer 120 includes multiple transmitters/receivers 410, 420, even if one transmitter/receiver 410, 420 is not adequately oriented to measure the blood flow, the remaining transmitters/receivers 410, 420 may adequately cover the carotid artery and be positioned to measure the flow of the blood cells. Furthermore, multiple transmitters/receivers 410, 420 reduce the risk of the rescuer improperly securing the Doppler pad 100 on the patient. Although the Doppler pad 100 illustrates where the rescuer should place the Doppler pad 100, even if the Doppler pad 100 is positioned slightly off, the multiplicity of transmitters/receivers 410, 420 ensures that at least one pair will be sufficiently positioned over the carotid artery to provide the means to detect the pulse, if any.

In a situation where CPR is required, usually it is expected that the patient's pulse in the patient would be either weak or none. Thus, using a single element transducer requires the rescuer to detect a good pulse from the patient in order to adequately align the Doppler Pad on the patient. However, in accordance with the present invention, the rescuer is not required to detect a good pulse but is required to place the pad in the vicinity of the carotid artery. Including multiple transmitters/receivers 410, 420 in the Doppler pad 100 provides a wider area to find the correct pulse signal.

In an exemplary embodiment, FIG. 5A illustrates a cross-sectional view of the Doppler pad 100 placed over the carotid artery transmitting continuous wave signals/acoustic waves at a constant frequency to the flow of red blood cells. Cross-sectional views of the adhesive pad 110, the transducer 120, and the transmitters/receivers 410, 420 are also shown. FIG. 5B illustrates the transmitted signals reflecting on the red blood cells or scattered from the red blood cells and return signals received by the receivers in the transducer 120. As illustrated in this figure, the return signals are at different frequencies. The defibrillator then calculates the associated Doppler shift and analyzes the frequency information from the return signals to determine the patient's pulse and to measure blood flow.

Figure 6:
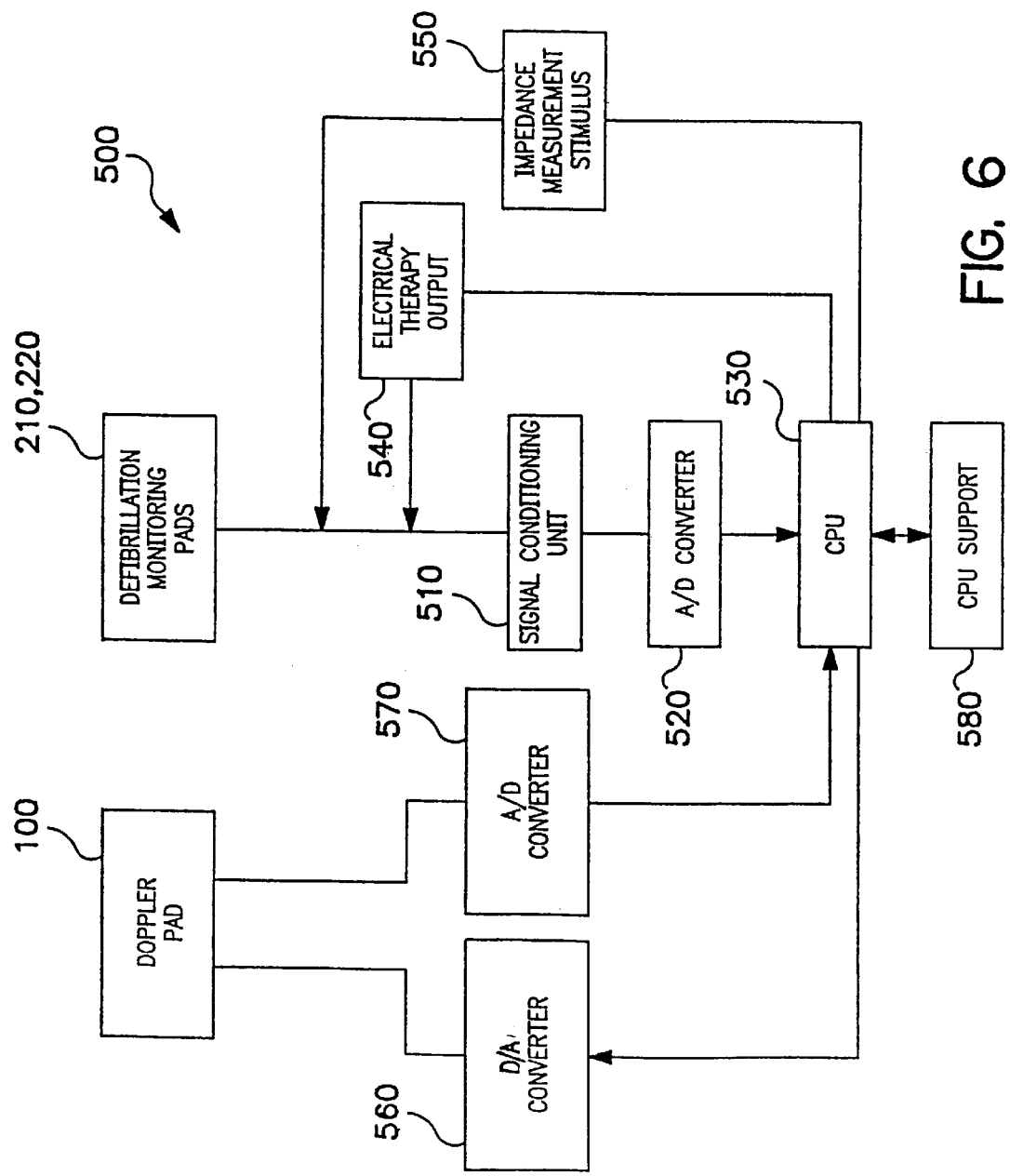
FIG. 6 is a general schematic diagram of a process performed by the cardiac resuscitation system of FIG. 2.

Referring to FIG. 6, this figure is a general schematic diagram of the process performed by the cardiac resuscitation system 200 of FIG. 2. Specifically, the defibrillation-monitoring pads 210, 220 detects and provide the ECG signals from the patient to the defibrillator. A signal conditioning unit 510 conditions the ECG signals by filtering the ECG signals. An A/D converter 520 converts the conditioned ECG signals to digital signals and provides the digital signals to a CPU 530 for determining whether defibrillation therapy should be applied to the patient, to be described in FIG. 7. The CPU 530 includes permanent or removable storage, such as magnetic and optical discs, RAM, ROM, etc., on which the process and data structures of the present invention can be stored and distributed. If the CPU 530 determines that a defibrillation therapy should be applied to the patient, for instance, if shock therapy is advised for the patient, then the CPU 530 would charge the energy storage capacitor (not shown) to apply an electrical therapy output pulse 540 or defibrillation therapy to the patient via the defibrillation-monitoring pads 210, 220. The CPU may further perform an impedance measurement stimulus 550 by sending very high frequency signals across the defibrillation-monitoring pads 210, 220. The impedance measurement stimulus is recorded in the signal conditioning unit 510 thereby providing the rescuer with the ability to determine if the defibrillation-monitoring pads 210, 220 are making good contact with the patient or if they are loose.

Furthermore, the CPU 530 outputs digital signals and transmits the digital signals to the Doppler pad 100 via a D/A converter 560. The analog signals from the D/A converter 560 trigger the transmitters in the Doppler pad 100 to emit CW signals to the blood cells in the carotid artery. The reflected signals are then received by the receivers in the Doppler pad 100 and an A/D converter 570 converts the reflected signals to a digital Doppler signal and provides the digital Doppler signal to the CPU 530 for further processing, to be described in FIG. 7. A CPU support 580 includes necessary hardware for a complete defibrillation system, that is, for example, memory, program storage, result storage, user interface elements (e.g., display buttons, etc.), and a power supply.

Figure 7:
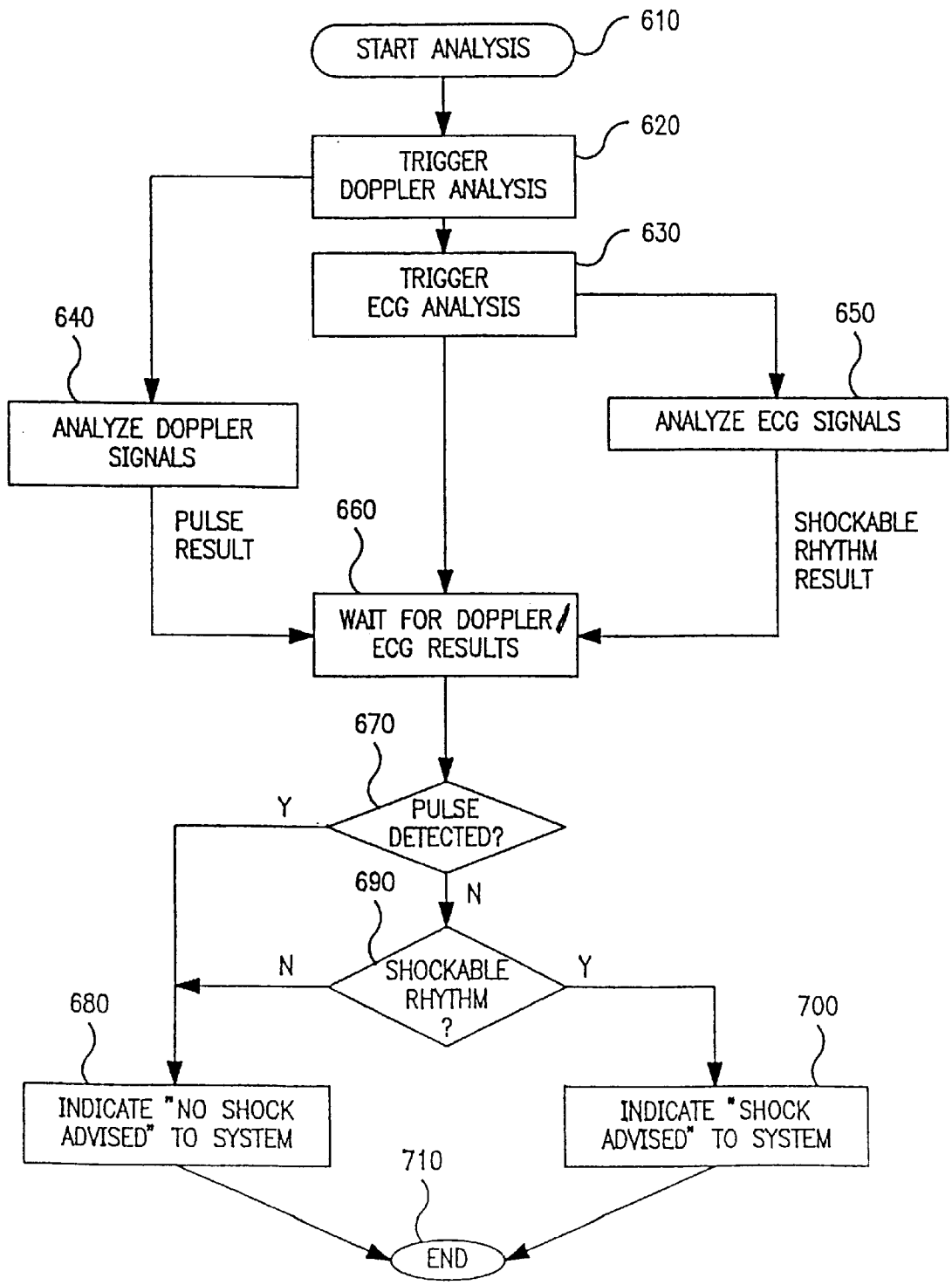
FIG. 7 is a schematic diagram of a process performed by the CPU of FIG. 6 determining whether the patient should be defibrillated, that is, whether shock therapy or noshock therapy is advised, in accordance with an exemplary embodiment of the present invention.

FIG. 7 illustrates a process performed by the CPU 530 determining whether the patient should be defibrillated, that is, whether or not a shock therapy is advised. The CPU 530 starts at operation 610 by clearing memories, setting initial flag conditions, etc., as is well known in the art. At operation 620, the CPU 530 triggers a Doppler analysis via the Doppler pad 100. At operation 630, the CPU 530 triggers an ECG analysis via the defibrillation-monitoring pads 210, 220. A person of ordinary skill in the art will appreciate that although operations 620 and 630 are described herein sequentially, both operations may be performed concurrently by the CPU 530.

At operation 640, the CPU 530 analyzes or monitors the return signals from the Doppler pad 100 (i.e., the Doppler signals) and the ECG signals from the defibrillation-monitoring pads 210, 220. The Doppler signals are indicative of the patient's pulse and thus, indicative of perfusion and is processed by the CPU 530 to measure blood flow. In an exemplary embodiment, the CPU 530 would receive the Doppler signals from the Doppler pad 100 and compare the Doppler signals with a threshold statistically appropriate with the Doppler signals received. The CPU 530 would be looking for a period of blood flow that exists above the threshold. If the Doppler signals are above the threshold, then the CPU 530 would determine that the Doppler signals are indicative of a pulse. Conversely, if the Doppler signals are below the threshold, then the Doppler signals are not considered a pulse but are considered to be background noise or low velocity residual flow. If the CPU 530 determines that there is a degree of predictability of the Doppler signals being above the threshold, then the CPU 530 determines that there is a rhythm.

At operation 650, the ECG signals from the defibrillation-monitoring pads 210, 220 are analyzed. The ECG signals are indicative of whether the patient's heart is undergoing a shockable rhythm. At operation 660, the CPU 530 waits for the Doppler signals and the ECG signals and integrates the signals for further processing. At operation 670, a determination is made whether a pulse is detected from the integrated signals. If a pulse is detected, the CPU 530 determines that there is cerebral perfusion and proceeds to operation 680. At operation 680, the CPU 530 indicates to the rescuer that "no shock is advised." From operation 680, the CPU 530 proceeds to operation 710 where the CPU 530 ends.

However, if at operation 670, a pulse is not detected, then the CPU 530 proceeds to operation 690. At operation 690, a determination is made as to whether a shockable rhythm is detected. If a shockable rhythm is detected, specifically that the heart is trying to beat but is not doing it properly, then the CPU 530 proceeds to operation 700. At operation 700, the CPU 530 indicates to the rescuer that "shock is advised." From operation 700, the CPU 530 proceeds to operation 710 where the CPU 530 ends. However, if at operation 690 a shockable rhythm is not detected, then the CPU 530 proceeds to operation 680 where the CPU 530 indicates to the rescuer that "no shock is advised." From operation 680, the CPU 530 proceeds to operation 710 where the CPU 530 ends.

If a stable signal is not available from either the Doppler analysis or the ECG analysis after a designated maximal waiting period, the system will determine if sufficient information is available to make an appropriate shock therapy decision, and will make such a decision in the absence of the unstable signal, or will indicate that a decision cannot be made.

In the normal operation of the cardiovascular system, the ECG signal corresponds to the activation of heart muscle, which causes ejection of blood from the heart into the arteries, causing flow in the arteries which can be detected by an appropriately placed Doppler flow detection system after the conduction delay. In a mechanically stable cardiovascular system, physiologically similar cardiac contractions, as indicated by similar ECG signals, should generate similar flow patterns in the arteries. If similar ECG patterns of contraction are detected and those contractions generate consistently similar flow patterns, and the flow is physiologically sufficient, then it would be expected that the cardiovascular system is performing well enough that a defibrillation shock is not indicated. Furthermore, the ECG or other signals available to a resuscitation device, such as those that indicate the start of external chest compressions, can be used as a temporal reference for flow measurements.

The CPU 530 may be also programmed to use the Doppler signal from the Doppler pad 100 to refine the decision of whether or not the shock therapy is advised for the patient when used with the SAED or the AED. Further, the CPU 530 may also perform an algorithm quantifying blood flow information from the pulse signal to refine the decision of whether or not the shock therapy is advised for the patient when used with the SAED or the AED.

Although a few preferred embodiments of the present invention have been shown and described, it would be appreciated by those skilled in the art that changes may be made in this embodiment without departing from the principles and spirit of the invention, the scope of which is defined in the claims and their equivalents.

What is claimed is:

1. A cardiac resuscitation apparatus, comprising:
    an adhesive Doppler pad detecting a pulse signal of a patient;
    defibrillation-monitoring pads, connected to the Doppler pad, detecting an ECG signal of the patient; and
    a processor integrating the pulse signal and the ECG signal to determine therefrom whether or not shock therapy is advised for the patient.

2. The cardiac resuscitation apparatus as recited in claim 1, wherein the ECG signal is indicative of whether the patient's heart is undergoing a shockable rhythm.

3. The cardiac resuscitation apparatus as recited in claim 2, wherein the Doppler pad further comprises a transducer comprising one of multiple transmitters and receivers, a single transmitter and multiple receivers, and multiple transmitters and a single receiver positioned at a predetermined orientation to detect the pulse signal of the patient indicative of cerebral perfusion and a duration of which is indicative of blood flow of the patient.

4. The cardiac resuscitation apparatus as recited in claim 3, wherein the processor determines from the integrated signals if a pulse of the patient is present, measures blood flow, and determines whether the shockable rhythm is present.

5. The cardiac resuscitation apparatus as recited in claim 1, wherein the Doppler pad and the defibrillation-monitoring pads are connected to the cardiac resuscitation apparatus via a single conductive cable.

6. The cardiac resuscitation apparatus as recited in claim 1, wherein the cardiac resuscitation apparatus is connected to an automated external programmable defibrillator (AED) or a semi-automated external programmable defibrillator (SAED).

7. The cardiac resuscitation apparatus as recited in claim 1, wherein each of the Doppler pad and the defibrillation-monitoring pads comprises a pictorial instruction providing guidance to a user as to placement of each pad on the patient.

8. A cardiac resuscitation system, comprising:
    an adhesive Doppler pad comprising one of multiple transmitters and receivers, a single transmitter and multiple receivers, and multiple transmitters and a single receiver integrated therein detecting a pulse signal of a patient;

defibrillation-monitoring pads detecting an ECG signal of the patient, wherein the adhesive Doppler pad and the defibrillation-monitoring pads are connected to a cardiac resuscitation apparatus via a single conductive cable; and a processor integrating the pulse signal and the ECG signal and determining therefrom if a pulse of the patient is present, measuring blood flow, and determining whether shockable rhythm is present.

9. The cardiac resuscitation apparatus as recited in claim 8, wherein the one of multiple transmitters and receivers, a single transmitter and multiple receivers, and multiple transmitters and a single receiver are positioned at a predetermined orientation to detect the pulse signal of the patient indicative of cerebral perfusion and a duration of which is indicative of blood flow of the patient.

10. The cardiac resuscitation apparatus as recited in claim 8, wherein the cardiac resuscitation apparatus is connected to an automated external programmable defibrillator (AED) or a semi-automated external programmable defibrillator (SAED).

11. The cardiac resuscitation apparatus as recited in claim 8, wherein each of the Doppler pad and the defibrillation-monitoring pads comprise a pictorial instruction providing guidance to user as to placement of each pad on the patient.

12. A cardiac resuscitation apparatus, comprising:
conductors connected into a single conductive cable and terminating in a Doppler pad and defibrillation-monitoring pads, wherein the conductors connect the Doppler pad and the defibrillation-monitoring pads to an automated external programmable defibrillator (AED) or a semi-automated external programmable defibrillator (SAED) as a unit.

13. A cardiac resuscitation system, comprising:
an adhesive Doppler pad comprising a piezo-electric transducer integrated therein and positioned relative to a carotid artery of a patient to detect a pulse signal using one of continuous wave signals, pulse signals, and phased array modalities, wherein the transducer comprises one of multiple transmitters and receivers, a single transmitter and multiple receivers, and multiple transmitters and a single receiver positioned at a predetermined orientation to detect the pulse signal indicative of cerebral perfusion and a duration of which is indicative of blood flow;

defibrillation-monitoring pads detecting a shockable rhythm of the patient, wherein the adhesive Doppler pad and the defibrillation-monitoring pads are connected to an automated external programmable defibrillator (AED) or a semi-automated external programmable defibrillator (SAED) via a single conductive cable and each of the Doppler pad and each of the Doppler pad and the defibrillation-monitoring pads comprise a pictorial instruction providing guidance to a user as to placement of each pad on the patient; and a processor determining from the integrated signals if a pulse of the patient is present, measuring blood flow, and determining whether the shockable rhythm is present to determine whether or not shock therapy is advised for the patient.

14. A cardiac resuscitation apparatus, comprising:
pulse detection means for detecting a pulse signal of a patient;
monitoring means, connected to the adhesive means, for detecting an ECG signal of the patient; and
processing means for integrating the pulse signal and the ECG signal to determine therefrom whether or not shock therapy is advised for the patient.

15. A cardiac resuscitation system, comprising:
pulse detection means comprising one of multiple transmitters and receivers, a single transmitter and multiple receivers, and multiple transmitters and a single receiver integrated therein for detecting a pulse signal of a patient;
monitoring means for detecting an ECG signal of the patient, wherein the adhesive means and the monitoring means are connected to a cardiac resuscitation apparatus via a single conductive cable; and
processing means for integrating the pulse signal and the ECG signal and determining therefrom if a pulse of the patient is present, measuring blood flow, and determining whether a shockable rhythm is present.

16. A cardiac resuscitation apparatus, comprising:
conductive means connected into a single conductive means and terminating in a Doppler pad and defibrillation-monitoring pads, wherein the conductive means connects the Doppler pad and the defibrillation-monitoring pads to an automated external programmable defibrillator (AED) or a semi-automated external programmable defibrillator (SAED) as a unit.

17. A cardiac resuscitation system, comprising:
pulse detection means comprising a piezo-electric transducer integrated therein and positioned relative to a carotid artery of a patient for detecting a pulse signal using one of continuous wave signals, pulse signals, and phased array modalities, wherein the transducer comprises one of multiple transmitters and receivers, a single transmitter and multiple receivers, and multiple transmitters and a single receiver positioned at a predetermined orientation to detect the pulse signal indicative of cerebral perfusion and a duration of which is indicative of blood flow;
defibrillation-monitoring means for detecting a shockable rhythm of the patient, wherein the adhesive means and the monitoring means are connected to an AED or SAED via a single conductive cable and each of the Doppler pad and the defibrillation-monitoring pads comprise a pictorial instruction providing guidance to a user as to placement of each pad on the patient; and
processing means for determining from the integrated signals if a pulse of the patient is present, measuring blood flow, and determining whether the shockable rhythm is present to determine whether or not shock therapy is advised for the patient.

18. A method in a cardiac resuscitation system, comprising:
detecting a pulse signal of a patient;
detecting an ECG signal of the patient;
integrating the pulse signal and the ECG signal; and
determining from the integrated signals whether or not shock therapy is advised to a patient.

19. The method as recited in claim 18, further comprising determining from the integrated signals if a pulse of the patient is present, measuring blood flow, and determining whether a shockable rhythm is present.

20. The method as recited in claim 18, further comprising positioning one of multiple transmitters and receivers, a single transmitter and multiple receivers, and multiple transmitters and a single receiver at a predetermined orientation to detect the pulse signal of the patient indicative of cerebral perfusion and a duration of which is indicative of blood flow of the patient.

21. A method in a cardiac resuscitation system, comprising:

detecting a pulse signal of a patient;

detecting an ECG signal of the patient; and integrating the pulse signal and the ECG signal and determining therefrom if a pulse is present, measuring blood flow, and determining whether a shockable rhythm is present.

22. The method as recited in claim 21, determining from the integrated signals whether or not shock therapy is advised to a patient.

23. The method as recited in claim 21, further comprising positioning one of multiple transmitters and receivers, a single transmitter and multiple receivers, and multiple transmitters and a single receiver at a predetermined orientation to detect the pulse signal of the patient indicative of cerebral perfusion and a duration of which is indicative of blood flow of the patient.

24. A method in a cardiac resuscitation system, comprising:

connecting an adhesive Doppler pad and defibrillation-monitoring pads to an AED or a SAED via a single conductive cable;

detecting a pulse signal of a patient via the adhesive Doppler pad comprising one of multiple transmitters and receivers, a single transmitter and multiple receivers, and multiple transmitters and a single receiver integrated therein;

detecting an ECG signal of the patient via the defibrillation-monitoring pads; and integrating the pulse signal and the ECG signal and determining therefrom if a pulse is present, measuring blood flow, and determining whether a shockable rhythm is present.

25. The method as recited in claim 24, further comprising positioning the one of multiple transmitters and receivers, a single transmitter and multiple receivers, and multiple transmitters at a predetermined orientation to detect the pulse signal of the patient indicative of cerebral perfusion and a duration of which is indicative of blood flow.

26. A method in a cardiac resuscitation system, comprising:

positioning an adhesive Doppler pad relative to a carotid artery of a patient to monitor a pulse signal;

positioning defibrillation-monitoring pads on the patient to monitor a signal indicative of a shockable rhythm;

integrating the pulse signal and the signal indicative of a shockable rhythm;

determining shock therapy is not advised for a patient when the integrated signal indicates that a pulse is detected or a shockable rhythm is not detected; and determining the shock therapy is advised for a patient when the integrated signal indicates that a pulse is not detected or a shockable rhythm is detected.

27. The method as recited in claim 26, further comprising processing the pulse signal to quantify blood flow in the patient.

28. The method as recited in claim 26, further comprising processing the integrated signal to refine the determination of whether or not the shock therapy is advised.

29. The method as recited in claim 26, further comprising providing an impedance measurement stimulus to determine if the defibrillation-monitoring pads are positioned so as to make good contact with the patient.

30. A method in a cardiac resuscitation system, comprising:

integrating a pulse signal and the signal indicative of a shockable rhythm of a patient;

determining shock therapy is not advised for a patient when the integrated signal indicates that a pulse is detected or a shockable rhythm is not detected; and determining the shock therapy is advised for a patient when the integrated signal indicates that a pulse is not detected or a shockable rhythm is detected.

31. The method as recited in claim 30, further comprising connecting an adhesive Doppler pad and defibrillation-monitoring pads to an AED or a SAED via a single conductive cable, wherein each of the Doppler pad and the defibrillation-monitoring pads comprise a pictorial instruction providing guidance to a user as to placement of each pad on the patient;

positioning the adhesive Doppler pad relative to a carotid artery of a patient to monitor the pulse signal; and positioning the defibrillation-monitoring pads on the patient to monitor the shockable rhythm.

32. A method in a cardiac resuscitation system, comprising:

connecting an adhesive Doppler pad and defibrillation-monitoring pads to an AED or a SAED via a single conductive cable, wherein each of the Doppler pad and defibrillation-monitoring pads comprise a pictorial instruction providing guidance to a user as to placement of each pad on the patient;

positioning the adhesive Doppler pad relative to a carotid artery of a patient to monitor a pulse signal, wherein the adhesive Doppler pad comprises one of multiple transmitters and receivers, a single transmitter and multiple receivers, and multiple transmitters and a single receiver positioned at predetermined orientation;

processing the pulse signal to quantify blood flow in the patient;

positioning defibrillation-monitoring pads on the patient to monitor a signal indicative of a shockable rhythm;

integrating the pulse signal and the signal indicative of a shockable rhythm;

determining shock therapy is nor advised for a patient when the integrated signal indicates that a pulse is detected or a shockable rhythm is not detected;

determining the shock therapy is advised for a patient when the integrated signal indicates that a pulse is not detected or a shockable rhythm is detected;

refining the integrated signals; and providing an impedance measurement stimulus to determine if the defibrillation-monitoring pads are positioned so as to make good contact with die patient.

33. A computer readable storage controlling a computer in a cardiac resuscitation system and comprising a process of detecting a pulse signal of a patient;

detecting an ECG signal of the patient;

integrating the pulse signal and the ECG signal; and determining from the integrated signals whether or not shock therapy is advised to a patient.

34. The computer readable storage as recited in claim 33, further comprising determining from the integrated signals if a pulse of the patient is present, measuring blood flow, and determining whether a shockable rhythm is present.

35. The computer readable storage as recited in claim 33, further comprising positioning one of multiple transmitters and receivers, a single transmitter and multiple receivers, and multiple transmitters and a single receiver at a predetermined orientation to detect the pulse signal of the patient indicative of cerebral perfusion and a duration of which is indicative of blood flow of the patient.

36. A computer readable storage controlling a computer in a cardiac resuscitation system and comprising
  a process of detecting a pulse signal of a patient;
  detecting an ECG signal of the patient; and
  integrating the pulse signal and the ECG signal and determining therefrom if a pulse is present, measuring blood flow, and determining whether a shockable rhythm is present.

37. The computer readable storage as recited in claim 36, determining from the integrated signals whether or not shock therapy is advised to a patient.

38. The computer readable storage as recited in claim 36, further comprising positioning one of multiple transmitters and receivers, a single transmitter and multiple receivers, and multiple transmitters and a single receiver at a predetermined orientation to detect the pulse signal of the patient indicative of cerebral perfusion and a duration of which is indicative of blood flow of the patient.

39. A computer readable storage controlling a computer in a cardiac resuscitation system and comprising
  a process of connecting an adhesive Doppler pad and defibrillation-monitoring pads to an AED or a SAED via a single conductive cable;
  detecting a pulse signal of a patient via the adhesive Doppler pad comprising one of multiple transmitters and receivers, a single transmitter and multiple receivers, and multiple transmitters and a single receiver integrated therein;
  detecting an ECG signal of the patient via the defibrillation-monitoring pads; and
  integrating the pulse signal and the ECG signal and determining therefrom if a pulse is present, measuring blood flow, and determining whether a shockable rhythm is present.

40. The computer readable storage as recited in claim 39, further comprising positioning the one of multiple transmitters and receivers, a single transmitter and multiple receivers, and multiple transmitters and a single receiver at a predetermined orientation to detect the pulse signal of the patient indicative of cerebral perfusion and a duration of which is indicative of blood flow.

41. A computer readable storage controlling a computer in a cardiac resuscitation system and comprising
  a process of positioning an adhesive Doppler pad relative to a carotid artery of a patient to monitor a pulse signal;
  positioning defibrillation-monitoring pads on the patient to monitor a signal indicative of a shockable rhythm;
  integrating the pulse signal and the signal indicative of a shockable rhythm;
  determining shock therapy is not advised for a patient when the integrated signal indicates that a pulse is detected or a shockable rhythm is not detected; and
  determining the shock therapy is advised for a patient when the integrated signal indicates that a pulse is not detected or a shockable rhythm is detected.

42. The computer readable storage as recited in claim 41, further comprising processing the pulse signal to quantify blood flow in the patient.

43. The computer readable storage as recited in claim 41, further comprising processing the integrated signal to refine the determination of whether or not the shock therapy is advised.

44. The computer readable storage as recited in claim 41, further comprising providing an impedance measurement stimulus to determine if the defibrillation-monitoring pads are positioned so as to make good contact with the patient.

45. A computer readable storage controlling a computer in a cardiac resuscitation system and comprising
  a process of integrating a pulse signal and a signal indicative of a shockable rhythm of a patient;
  determining shock therapy is not advised for a patient when the integrated signal indicates that a pulse is detected or a shockable rhythm is not detected; and
  determining the shock therapy is advised for a patient when the integrated signal indicates that a pulse is not detected or a shockable rhythm is detected.

46. The computer readable storage as recited in claim 45, further comprising
  connecting an adhesive Doppler pad and defibrillation-monitoring pads to an AED or a SAED via a single conductive cable, wherein each of the Doppler pad and the defibrillation-monitoring pads comprise a pictorial instruction providing guidance to a user as to placement of each pad on the patient;
  positioning the adhesive Doppler pad relative to a carotid artery of a patient to monitor the pulse signal; and
  positioning the defibrillation-monitoring pads on the patient to monitor the shockable rhythm.

47. A computer readable storage controlling a computer in a cardiac resuscitation system and comprising
  a process of connecting an adhesive Doppler pad and defibrillation-monitoring pads to an AED or a SAED via a single conductive cable, wherein each of the Doppler pad and defibrillation-monitoring pads comprise a pictorial instruction providing guidance to a user as to placement of each pad on the patient;
  positioning the adhesive Doppler pad relative to a carotid artery of a patient to monitor a pulse signal, wherein the adhesive Doppler pad comprises one of multiple transmitters and receivers, a single transmitter and multiple receivers, and multiple transmitters and a single receiver positioned at predetermined orientation;
  processing the pulse signal to quantify blood flow in the patient;
  positioning defibrillation-monitoring pads on the patient to monitor a signal indicative of a shockable rhythm;
  integrating the pulse signal and the signal indicative of a shockable rhythm;
  determining shock therapy is not advised for a patient when the integrated signal indicates that a pulse is detected or a shockable rhythm is not detected;
  determining the shock therapy is advised for a patient when the integrated signal indicates that a pulse is not detected or a shockable rhythm is detected;
  refining the integrated signals; and
  providing an impedance measurement stimulus to determine if the defibrillation-monitoring pads are positioned so as to make good contact with the patient.

* * * * *